United States Patent [19]

Martin et al.

[11] 4,007,167

[45] Feb. 8, 1977

[54] ANTIBIOTIC BM123 AND PRODUCTION THEREOF

[75] Inventors: John Henry Edward James Martin; Homer David Tresner, both of New City, N.Y.; John Norman Porter, Ramsey, N.J.

[73] Assignee: American Cyanamid Company, Stamford, Conn.

[22] Filed: Aug. 21, 1975

[21] Appl. No.: 606,634

Related U.S. Application Data

[63] Continuation-in-part of Ser. No. 513,358, Oct. 9, 1974, abandoned, which is a continuation-in-part of Ser. No. 458,274, April 5, 1974, abandoned, which is a continuation-in-part of Ser. No. 297,173, Oct. 12, 1972, abandoned.

[52] U.S. Cl. ................................ 536/17; 195/96; 424/181
[51] Int. Cl.$^2$ ................ C07H 17/02; C07H 15/02
[58] Field of Search ........................... 260/210 AB

[56] References Cited

UNITED STATES PATENTS

| 3,784,541 | 1/1974 | Culbertson et al. | 260/210 AB |
| 3,843,449 | 10/1974 | Kawaguchi et al. | 260/210 AB |

Primary Examiner—Johnnie R. Brown
Attorney, Agent, or Firm—Edward A. Conroy, Jr.

[57] ABSTRACT

This disclosure describes 5 new antibacterial agents designated $BM123\alpha$, $BM123\beta_1$, $BM123\beta_2$, $BM123\gamma_1$, and $BM123\gamma_2$ produced in a microbiological fermentation under controlled conditions using a new strain of an undetermined species of Nocardia and mutants thereof. The new antibacterial agents are active against a variety of microorganisms and thus are useful in inhibiting the growth of such bacteria wherever they may be found.

5 Claims, 9 Drawing Figures

INFRARED ABSORPTION SPECTRUM OF BMI23Y₁ IN A KBr DISC

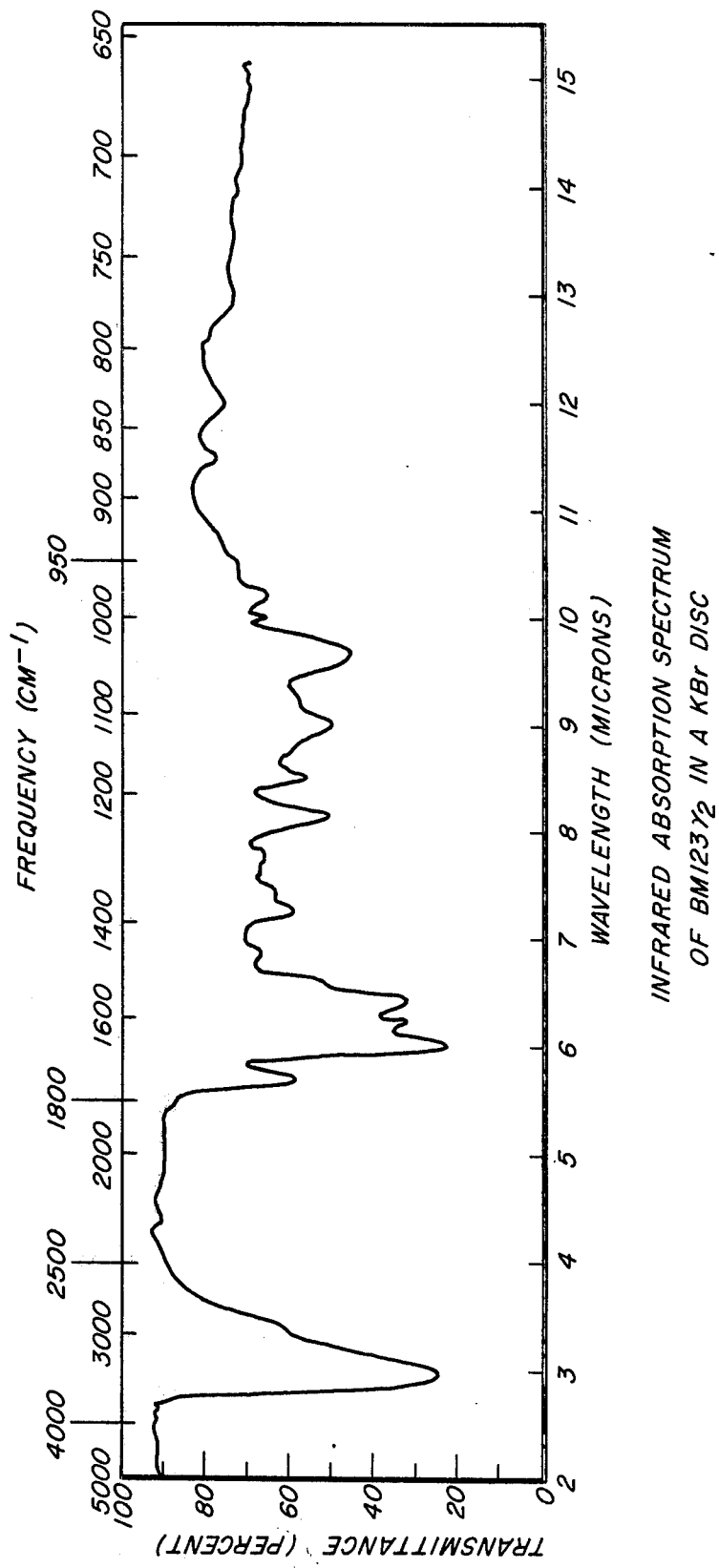

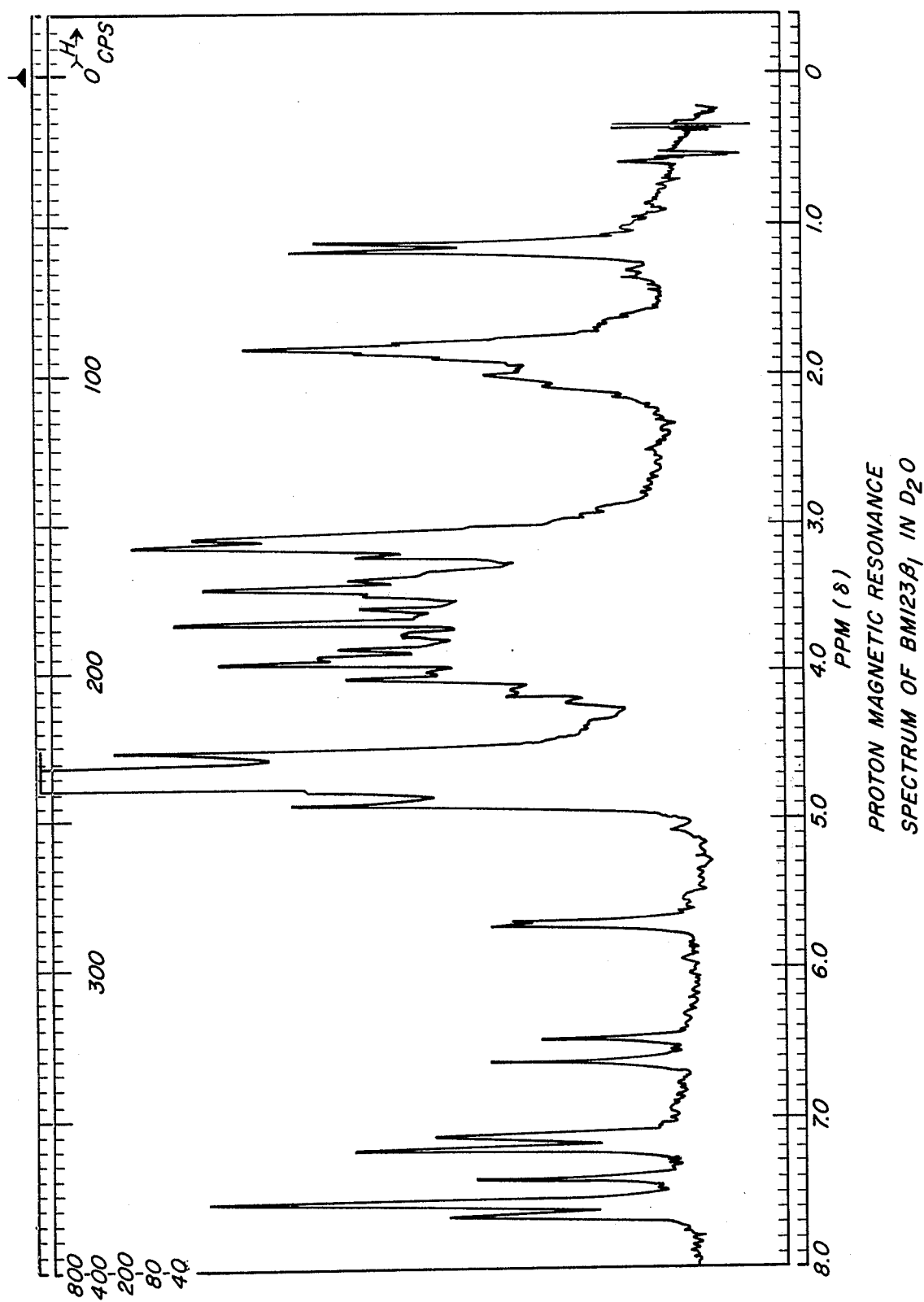

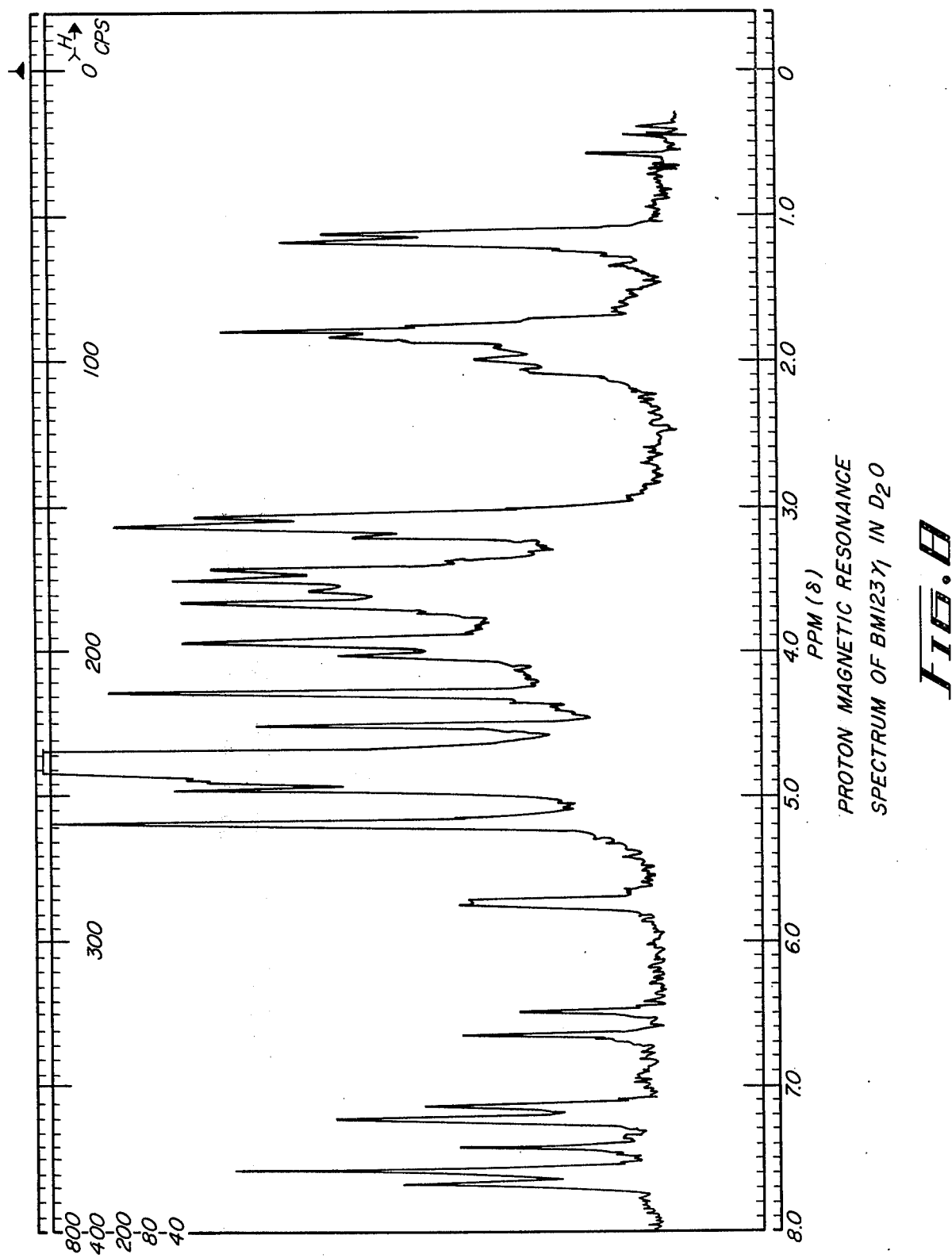
FIG. 8 PROTON MAGNETIC RESONANCE SPECTRUM OF BM123Y₁ IN D₂O

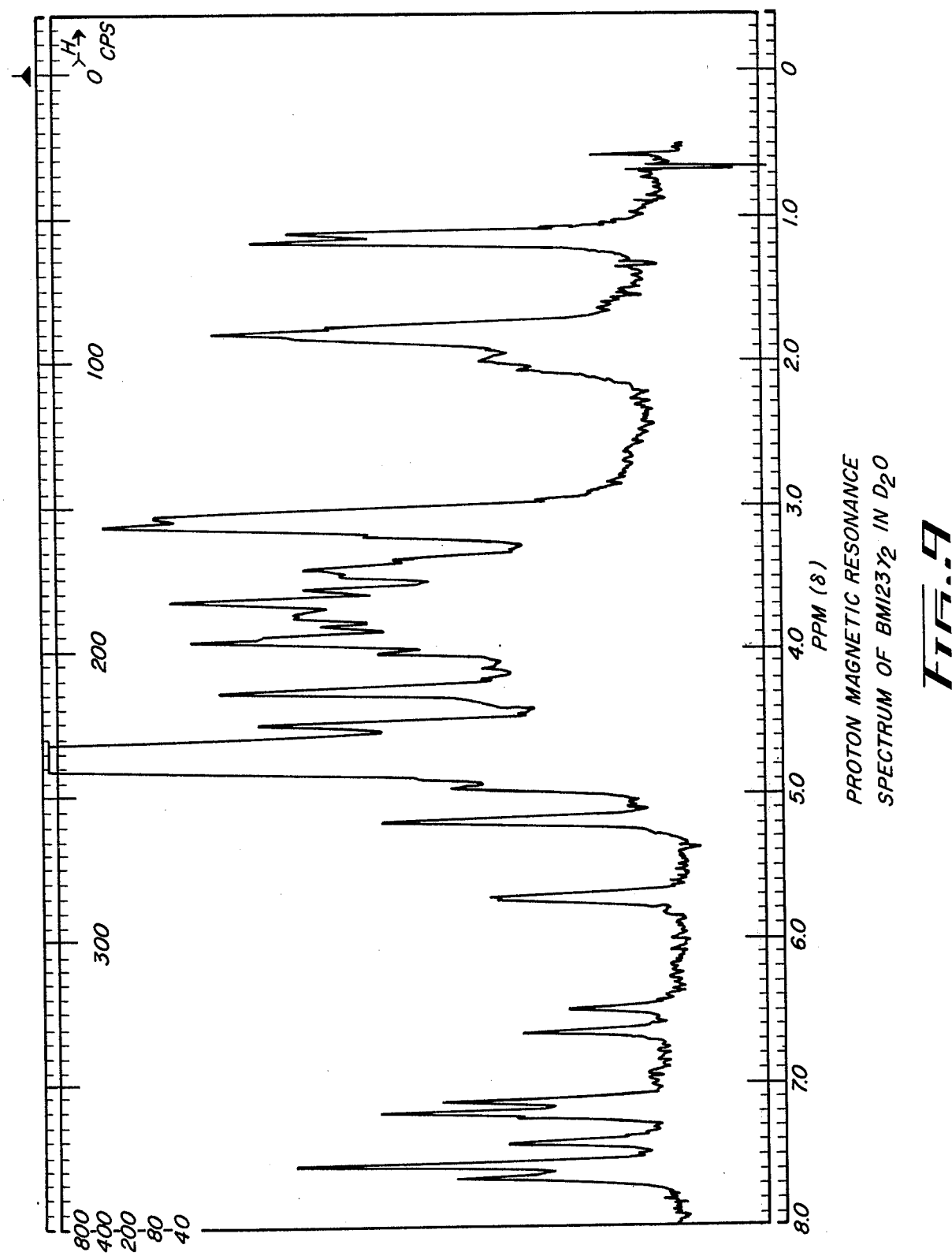

ANTIBIOTIC BM123 AND PRODUCTION THEREOF

CROSS REFERENCE TO RELATED APPLICATIONS

This application is a continuation-in-part of our co-pending application Ser. No. 513,358, filed Oct. 9, 1974, now abandoned which is a continuation-in-part of our abandoned application Ser. No. 458,274, filed Apr. 5, 1974, which is a continuation-in-part of our abandoned application Ser. No. 297,173, filed Oct. 12, 1972.

BRIEF SUMMARY OF THE INVENTION

This invention relates to 5 new antibacterial agents designated BM123α, BM123β$_1$, BM123β$_2$, BM123γ$_1$, and BM123γ$_2$; to their production by fermentation, to methods for their recovery and concentration from crude solutions, and to processes for their purification. The present invention includes within its scope the antibacterial agents in dilute forms, as crude concentrates, and in pure crystalline forms. The effects of the new antibacterial agents on specific microorganisms, together with their chemical and physical properties, differentiate them from previously described antibacterial agents.

Antibacterial BM123α may be represented by the following structural formula (I):

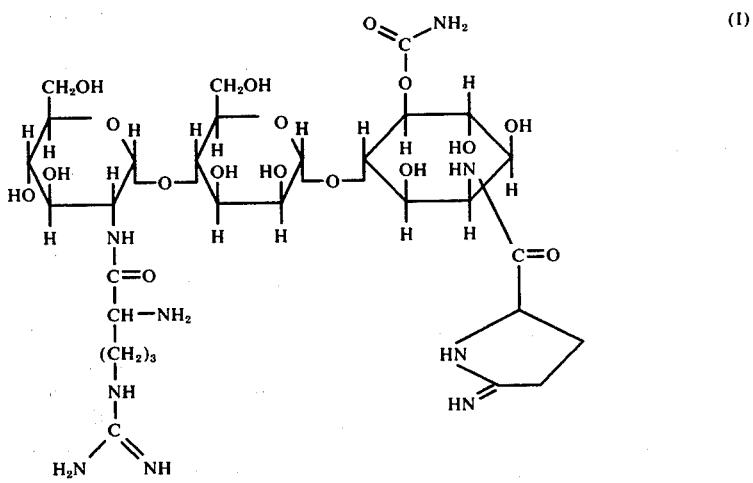

Antibacterial BM123β$_1$ may be represented by the following structural formula (II):

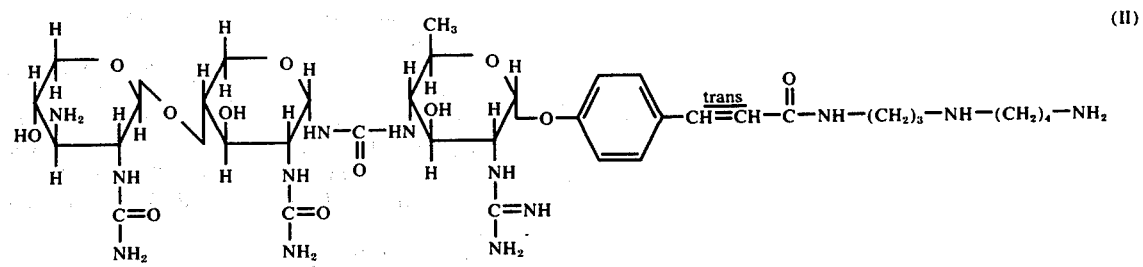

The molecular structure of antibacterial BM123β$_2$ is unknown at the present time.

Antibacterials BM123γ$_1$ and BM123γ$_2$ are structural isomers and each may be represented by the following structural formulae (III and IV respectively):

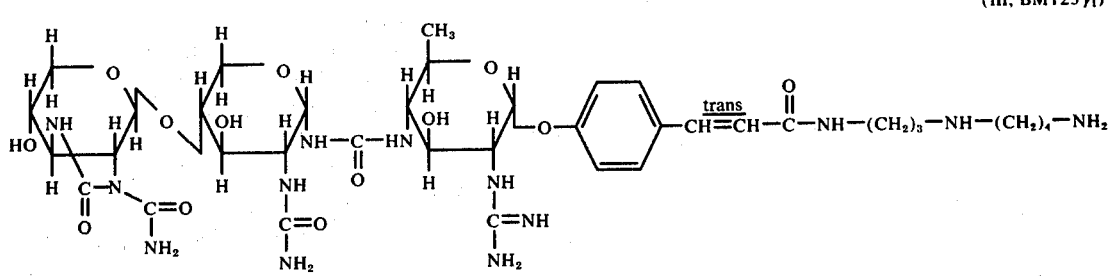

-continued

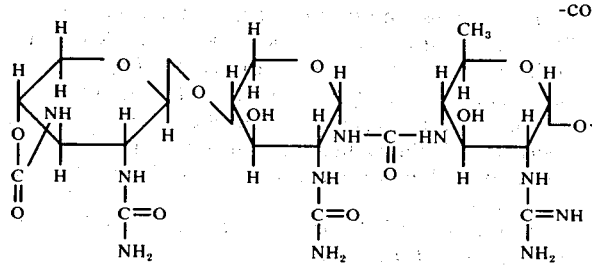 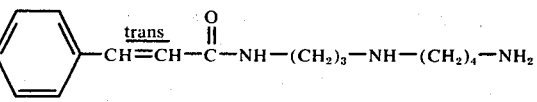

The novel antibacterial agents of the present invention are organic bases and thus are capable of forming acid-addition salts with a variety of organic and inorganic salt-forming reagents. Thus, acid-addition salts, formed by admixture of the antibacterial free base with up to three equivalents of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the antibacterial agents of the present invention are, in general, crystalline solids relatively soluble in water, methanol and ethanol but are relatively in-soluble in non-polar organic solvents such as diethyl ether, benzene, toluene, and the like. For purposes of this invention, the antibacterial free bases are equivalent to their non-toxic acid-addition salts. Hereinafter BM123$\beta$ refers to a mixture in any proportions of BM123$\beta_1$ and BM123$\beta_2$, and BM123$\gamma$ refers to a mixture in any proportions of BM123$\gamma_1$ and BM123$\gamma_2$.

DETAILED DESCRIPTION OF THE INVENTION

Figure 1:
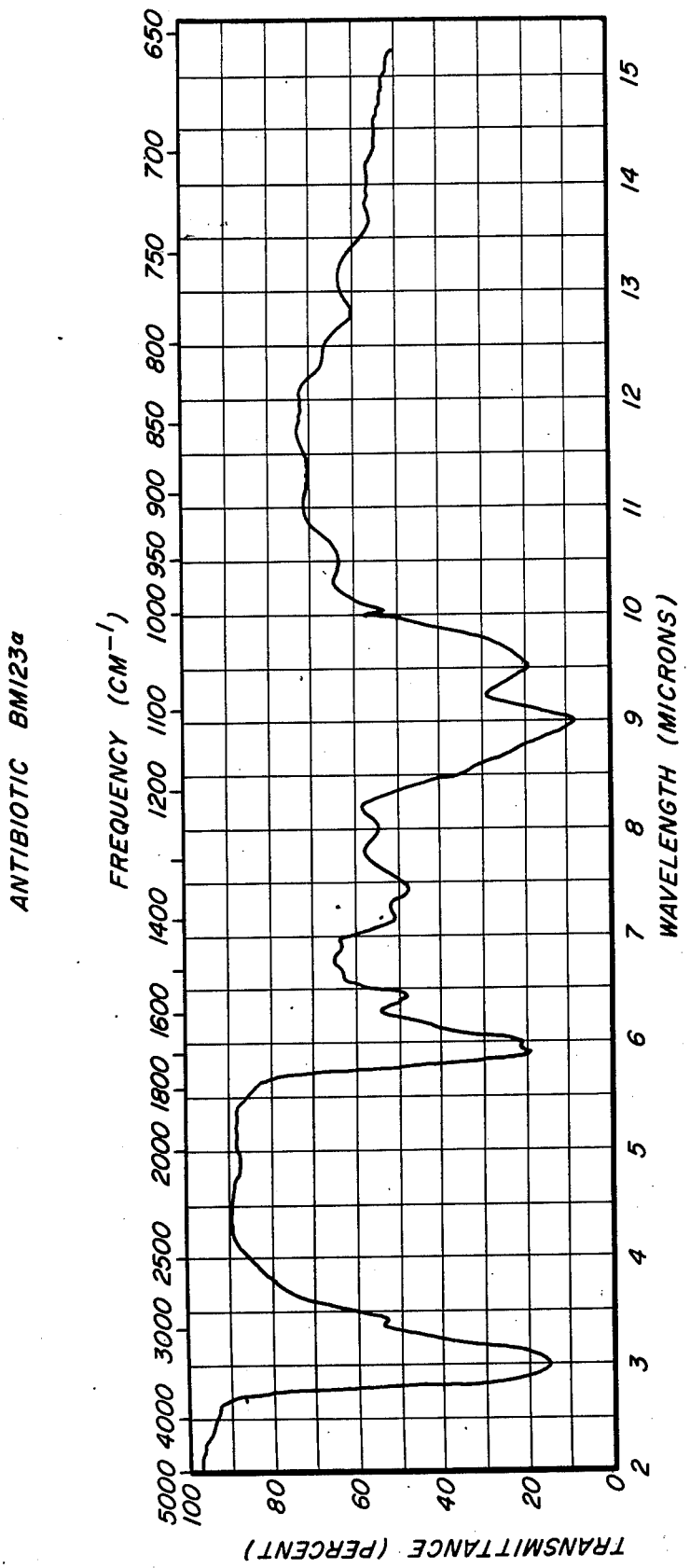

The new antibacterial agents which we have designated BM123$\alpha$, BM123$\beta_1$, BM123$\beta_2$, BM123$\gamma_1$, and BM123$\gamma_2$ are formed during the cultivation under controlled conditions of a new strain of an undetermined species of Nocardia. This new antibiotic producing strain was isolated from a garden soil sample collected at Oceola, Iowa and is maintained in the culture collection of the Lederle Laboratories Division, American Cyanamid Company, Pearl River, N.Y. as Culture No. BM123. A viable culture of the new microorganism has been deposited with the Culture Collection Laboratory, Northern Utilization Research and Development Division, U.S. Department of Agriculture, Peoria, Ill., and has been added to its permanent collection. It is freely available to the public in this depository under its accession number NRRL 5646.

The following is a general description of the microoganism Nocardia sp. NRRL 5646, based on diagnostic characteristics observed. Observations were made of the cultural, physiological, and morphological features of the organism in accordance with the methods detailed by Shirling and Gottlieb, Internat. Journ. of Syst. Bacteriol. 16:313–340 (1966). The chemical composition of the culture was determined by the procedures given by Lechevalier et al., Advan. Appl. Microbiol. 14:47–72 (1971). The underscored descriptive colors and color chip designations are taken from Jacobson et al., Color Harmony Manual, 3 rd. edit. (1948), Container Corp. of America, Chicago, Ill. Descriptive details are recorded in Tables I through V below.

Amount of Growth

Moderate on yeast extract, asparagine dextrose, Benedict's, Bennett's, potato dextrose and Weinstein's agars; light on Hickey and Tresner's, tomato paste oatmeal and pablum agars and a trace of growth on inorganic salts-starch, Kuster's oatflake, Czapek's solution and rice agars.

Aerial Mycelium

Aerial mycelium whitish when present; produced only on yeast extract, asparagine dextrose, Benedict's, Bennett's and potato dextrose agars.

Soluble Pigments

No soluble pigments produced.

Reverse Color

Colorless to yellowish shades.

Miscellaneous Physiological Reactions

No liquefaction of gelatin; nitrates reduced to nitrites in 7 days; melanoid pigments not formed on peptone-iron agar; no peptonization or curd formation in purple milk; NaCl tolerance in yeast extract agar $\leqq$ 4% but <7%; optimal growth temperature 32° C. Carbon source utilization, according to the Pridham and Gottlieb method [J. Bacteriol. 56:107–114 (1948)] as follows: Good utilization of glycerol, salicin, d-trehalose and dextrose; fair utilization of i-inositol; and poor to non-utilization of d-fructose, maltose, adonitol, l-arabinose, lactose, d-mannitol, d-melibiose, d-raffinose, l-rhamnose, sucrose and d-xylose.

Chemical Composition

The organism belongs to cell wall type IV, i.e., contains meso-2,6-diaminopimelic acid and has a type A whole-cell sugar pattern, i.e., contains arabinose and galactose. Methylated whole cell extracts, when subjected to gas chromatography, showed fatty acid patterns similar to those produced by Nocardia asteroides ATCC 3308.

Micromorphology

Aerial mycelium arises from substrate mycelium as sparingly branched moderately long flexuous elements that commonly terminate in elongated primitive spirals. The flexuous elements are irregularly segmented into short elliptical to cyclindrical sections (spores?) which disarticulate readily. The spiral terminal portions are less conspicuously segmented. Segments generally range 0.8–1.7 $\mu$m $\times$ 0.3–0.5 $\mu$m, averaging 0.4 $\mu$m $\times$ 1.2 $\mu$m.

Diagnosis

The morphological characteristics of Culture No. BM123 are difficult to observe and interpret because of the poor development of aerial mycelium on most media. Hence, considerable importance is attached, out of necessity, to the chemical analysis in determining the generic relationship of the organism. On the basis of the system proposed by Lechevalier et al., Culture No. BM123 contains meso-2,6-diaminopimelic acid in its whole cells and sugar analysis shows arabinose and galactose to be present. Therefore, the culture belongs to cell wall type IV. A comparison of the gas chromatography pattern of Culture No. BM123 with that of Nocardia asteroides ATCC 3308 showed the two to be remarkably similar. Other characteristics of Culture No. BM123 that are in keeping with the Nocardia concept, are its fragmenting aerial growth on some media and the total absence of aerial growth on most media. In view of the lack of adequate criteria for the characterization of Nocardia to the species level, no attempt has been made to make this determination.

Therefore, Culture No. BM123 will be considered an undetermined species of Nocardia until such a diagnosis is feasible.

TABLE I

Cultural Characteristics of *Nocardia sp.* NRRL 5646
Incubation: 14 days   Temperature: 32° C.

| MEDIUM | AMOUNT OF GROWTH | AERIAL MYCELIUM AND/OR SPORES | SOLUBLE PIGMENT | REVERSE COLOR | REMARKS |
|---|---|---|---|---|---|
| Yeast Extract Agar | Moderate | Aerial mycelium whitish, light. | None | Mustard (3 le) | Darkened areas in substrate mycelium. Coremia formed in surface mycelium. |
| Hickey and Tresner's Agar | Light | No aerial mycelium | None | Colorless to yellowish-green | Peripheral areas of colonies becoming olive-green |
| Asparagine dextrose Agar | Moderate | Trace of whitish aerial mycelium. | None | Amber (3 lc) | Surface lightly wrinkled |
| Benedict's Agar | Moderate | Aerial mycelium whitish, light. | None | Nude Tan (4 gc) | Coremia abundantly formed on surface mycelium. |
| Bennett's Agar | Moderate | Trace of whitish aerial mycelium | None | Camel (3 ie) | Surface lightly wrinkled. |
| Inorganic Salts-starch Agar | Trace | No aerial mycelium | None | Colorless | |
| Kuster's Oatflake Agar | Trace | No aerial mycelium | None | Colorless | |
| Czapek's Solution Agar | Trace | No aerial mycelium | None | Colorless | |
| Potato dextrose Agar | Moderate | Aerial mycelium whitish, light. | None | Camel (3 ie) | |
| Tomato Paste Oatmeal Agar | Light | No aerial mycelium | None | Colorless | |
| Pablum Agar | Light | No aerial mycelium | None | Colorless | |
| Rice Agar | Trace | No aerial mycelium | None | Colorless | |
| Weinstein's Agar | Moderate | No aerial mycelium | None | Colorless to yellowish | |
| Kuster's Oatflake Agar | Trace | No aerial mycelium | None | Colorless | |

TABLE II

Micromorphology of *Nocardia sp* NRRL 5646

| Medium | Aerial Mycelium and/or Sporiferous Structures |
|---|---|
| Yeast Extract Agar | Aerial mycelium arises from substrate mycelium as sparingly branched, flexuous elements that commonly terminate in elongated primitive spirals. The flexuous elements are irregularly segmented into short sections (spores?) which disarticulate readily. The spiral terminal portions are less conspicuously segmented. Segments generally range 0.8–1.7 μm × 0.3–0.5 μm, averaging 0.4 μm × 1.2 μm. |

TABLE III

Miscellaneous Physiological Reaction of *Nocardia sp.* NRRL 5646

| MEDIUM | INCUBATION PERIOD | AMOUNT OF GROWTH | PHYSIOLOGICAL REACTION |
|---|---|---|---|
| Gelatin | 7 days | Light | No liquefaction |
| Gelatin | 14 days | Good | No liquefaction |
| Organic Nitrate Broth | 7 days | Good | Nitrates reduced to nitrites |
| Organic Nitrate Broth | 14 days | Good | Nitrates reduced to nitrites |
| Peptone-iron Agar | 24–48 hours | Good | No melanin pigments produced |
| Purple Milk | 7 days | Good | No peptonization or curd formation |
| Yeast extract Agar plus (4, 7, 10 and 13%) NaCl | 7 days | Moderate | NaCl tolerance 4% but <7% |

TABLE IV

Carbon Source Utilization Pattern of *Nocardia sp.* NRRL 5646

Incubation: 10 days   Temperature: 32° C.

| Carbon Source | Utilization |
|---|---|
| Adonitol | 0 |
| l-Arabinose | 0 |
| Glycerol | 3 |
| d-Fructose | 1 |
| i-Inositol | 2 |
| Lactose | 0 |
| d-Mannitol | 0 |
| Salicin | 2 |
| d-Melibiose | 0 |
| d-Raffinose | 0 |
| Rhamnose | 0 |
| Maltose | 1 |
| Sucrose | 0 |
| d-Trehalose | 3 |
| d-Xylose | 0 |

TABLE IV-continued

Carbon Source Utilization Pattern of *Nocardia sp.* NRRL 5646
Incubation: 10 days     Temperature: 32° C.

| Carbon Source | Utilization |
|---|---|
| Dextrose | 3 |
| Negative Control | 0 |

3-Good Utilization
2-Fair Utilization
1-Poor Utilization
0-No Utilization

TABLE V

Chemical Composition of *Nocardia sp.* NRRL 5646

| Cell Wall Type | Major Constituents |
|---|---|
| Type IV | meso-DAP, arabinose, galactose |

It is to be understood that for the production of these new antibacterial agents the present invention is not limited to this particular organism or to organisms fully answering the above growth and microscopic characteristics which are given for illustrative purposes only. In fact, it is desired and intended to include the use of mutants produced from this organism by various means such as exposure to X-radiation, ultraviolet radiation, nitrogen mustard, actinophages, and the like. Viable cultures of two such mutant strains have been deposited with the Culture Collection Laboratory, Northern Utilization Research and Development Division, U.S. Department of Agriculture, Peoria, Ill., and have been added to its permanent collection under their accession numbers NRRL 8050 and NRRL 8103. Although the cultural, physiological, and morphological features of NRRL 8050 and NRRL 8103 are substantially the same as those of NRRL 5646; NRRL 8103 produces enhanced amounts of BM123α during aerobic fermentation whereas NRRL 8050 produces enhanced amounts of BM123γ during aerobic fermentation. Also, NRRL 8050 varies from the parent NRRL 5646 as follows:
  a. slower reduction of nitrates to nitrites; and
  b. production of a rosewood tan mycelial pigment on Bennett's and yeast extract agars.

Preliminary isolation, thin layer chromatography, and paper chromatography experiments have shown that five antibiotics are produced during the aerobic fermentation of Nocardia sp. NRRL 5646 as heretofore designated. Nutrient media studies resulted in two types of mashes: an alpha type mash which produces primarily BM123α; and a gamma type mash which produces primarily BM123γ$_1$ and BM123γ$_2$ along with lesser amounts of BM123α, BM123β$_1$ and BM123β$_2$.

The antibacterial agents were compared in vitro using a variety of gram positive and gram negative bacteria as well as *M. smegmatis* by the standard agar dilution procedure. The results are reported as minimal inhibitory concentrations (mcg./ml.) in Table VI. Gentamicin sulfate was run as a comparison.

TABLE VI

| Organism | Minimal Inhibitory Concentration (mcg./ml.) | | | | | | |
|---|---|---|---|---|---|---|---|
| | BM123α | BM123β | BM123β$_1$ | BM123γ | BM123γ$_1$ | BM123γ$_2$ | Gentamicin Sulfate |
| *Mycobacterium smegmatis* ATCC 607 | 5 | 5 | 2.5 | 0.25 | 0.1 | 0.25 | 0.1 |
| *Staphylococcus aureus* Rose ATCC 14154 | 100 | 2.5 | 1 | 0.25 | 0.25 | 0.25 | 0.1 |
| *Staphylococcus aureus* Smith ATCC 13709 | 20 | 1 | 0.5 | 0.25 | 0.1 | 0.25 | 0.05 |
| *Staphylococcus aureus* 4050B122-3 | 100 | 2.5 | 2.5 | 0.25 | 0.25 | 0.5 | 0.25 |
| *Bacillus cereus* ATCC 9634 | 100 | 25 | 2.5 | 1 | 0.25 | 0.5 | 0.25 |
| *Bacillus globigii* | 10 | 0.25 | 0.25 | 0.25 | 0.1 | 0.1 | 0.025 |
| *Bacillus subtilis* No. 17 Stansly R-78 | 10 | 0.25 | 0.25 | 0.25 | 0.1 | 0.1 | 0.025 |
| *Bacillus subtilis* No. 18 Stansly R-76 | 20 | 5 | 2.5 | 0.5 | 0.25 | 0.25 | 0.1 |
| *Corynebacterium xerosis* NRRL B-1397 | 10 | 5 | 2.5 | 0.25 | 0.25 | 0.25 | 0.025 |
| *Streptococcus faecalis* GK | >200 | >100 | >100 | 5 | 2.5 | 2.5 | 2.5 |
| *Sarcina lutea* ATCC 9341 | 50 | 10 | 2.5 | 1 | 0.5 | 1 | 0.25 |
| *Enterobacter aerogenes* 75 | 10 | 0.5 | 0,5 | 0.25 | 0.1 | 0.1 | 0.1 |
| *Escherichia coli* U-311 | 5 | 0.5 | 0.25 | 0.25 | 0.1 | 0.1 | 0.05 |
| *Escherichia coli* No. 29 | 5 | 0.5 | 0.25 | 0.25 | 0.05 | 0.1 | 0.05 |
| *Klebsiella pneumoniae* AD | 5 | 0.25 | 0.25 | 0.1 | 0.05 | 0.05 | 0.05 |
| *Proteus mirabilis* ATCC 4671 | 50 | 2.5 | 0.5 | 0.25 | 0.25 | 0.25 | 0.25 |
| *Proteus morganii* ATCC 8019 | 5 | 1 | 0.5 | 0.25 | 0.1 | 0.1 | 0.1 |
| *Proteus vulgaris* ATCC 9484 | 5 | 0.5 | 0.25 | 0.25 | 0.1 | 0.1 | 0.1 |
| *Pseudomonas aeruginosa* ATCC 10145 | 200 | 50 | 25 | 5 | 2.5 | 5 | 2.5 |
| *Pseudomonas aeruginosa* 1A7 | >200 | >100 | 100 | 10 | 5 | 10 | 5 |
| *Salmonella gallinarum* 605 | 5 | 0.5 | 0.5 | 0.1 | 0.1 | 0.1 | 0.05 |
| *Salmonella typhosa* ATCC 6539 | 5 | 0.5 | 0.25 | 0.1 | 0.05 | 0.05 | 0.1 |
| *Shigella shiga* | 50 | 2.5 | 2.5 | 0.25 | 0.25 | 0.25 | 0.25 |

The antibacterial agents BM123α, BM123β, and BM123γ are also active in vivo against a variety of organisms. These new antibacterials are thereby potentially useful as therapeutic agents in treating bacterial infections in mammals. These new antibacterials can be expected to be usefully employed for treating or controlling bacterial infections by parenteral administration.

The usefulness of these new antibacterial agents is demonstrated by their ability to control systemic lethal infections in mice. These new substances show high in vivo antibacterial activity in mice against *Proteus mirabilis* ATCC 4671, *Klebsiella pneumoniae* AD, and *Escherichia coli* US311 when administered by a single subcutaneous dose to groups of Carworth Farms CF-1 mice, weight about 20 gm., infected intraperitoneally with a lethal dose of these bacteria in $10^{-1.6}$, $10^{-4}$ and $10^{-3}$ trypticase soy broth TSP dilutions, respectively, of a 5 hour TSP blood culture.

Table VII, below, illustrates the in vivo antibacterial activity of BM123α, BM123β, and BM123γ against these three bacteria.

TABLE VII

| Single Subcutaneous Dose mg./kg. | Alive/Total Mice Tested, 7 Days After Infection | | |
|---|---|---|---|
| | BM123α | BM123β | BM123γ |
| | *Proteus Mirabilis* | | |
| 512 | 5/5 | | |
| 128 | 3/5 | | |
| 32 | 2/5 | 5/5 | |

TABLE VII-continued

| Single Subcutaneous Dose mg./kg. | Alive/Total Mice Tested, 7 Days After Infection | | |
|---|---|---|---|
| | BM123α | BM123β | BM123γ |
| 16 | | 5/5 | |
| 8 | 0/5 | 3/5 | |
| 4 | | 1/5 | 20/20 |
| 2 | | 0/5 | 9/25 |
| 1 | | | 2/20 |
| 0.5 | | | 0/25 |
| Infected, nontreated controls | | 68/70 Mice Died within 1 day after infection | |
| *Klebsiella pneumoniae* | | | |
| 512 | 4/5 | | |
| 128 | 0/5 | | |
| 64 | | | |
| 32 | 0/5 | 7/10 | |
| 16 | | 10/10 | |
| 8 | | 8/10 | |
| 4 | | 0/10 | 5/5 |
| 2 | | | 8/10 |
| 1 | | | 4/10 |
| 0.5 | | | 0/10 |
| Infected, nontreated controls | | 20/20 Mice died within 2 days after infection | |
| *Escherichia coli* | | | |
| 512 | 5/5 | | |
| 128 | 5/5 | | |
| 32 | 1/5 | | |
| 8 | | 9/10 | |
| 4 | | 5/10 | 10/10 |
| 2 | | 3/10 | 9/10 |
| 1 | | 1/10 | 5/10 |
| 0.5 | | 0/5 | 4/10 |
| 0.25 | | | 3/10 |
| 0.12 | | | 1/5 |
| Infected, nontreated controls | | 18/20 Mice died within 3 days after infection | |

Fermentation Process Selected to Product Primarily BM123α

Cultivation of *Nocardia sp.* NRRL 8103 may be carried out in a wide variety of liquid culture media. Media which are useful for the production of this novel antibacterial agent include an assimilable source of carbon such as starch, sugar, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc.; are supplied as impurities of other constituents of the media. Aeration in tanks and bottles is provided by forcing sterile air through or onto the surface of the fermenting medium. Further agitation in tanks is provided by a mechanical impeller. An antifoaming agent such as lard oil may be added as needed.

Inoculum Preparation for BM123α

Shaker flask inoculum of *Nocardia sp.* NRRL 8103 is prepared by inoculating 100 ml. of sterile liquid medium in 500 ml. flasks with scrapings or washings of spores from an agar slant of the culture. The following is an example of a suitable medium:
Beef extract 3.0 gm.
Bacto-tryptone 5.0 gm.
Yeast extract 5.0 gm.
Starch 24.0 gm.
Dextrose 1.0 gm.
Water to 1,000 ml.
Adjust medium pH to 7.0 with NaOH The flasks are incubated at a temperature from 25°–29° C., preferably 28° C., and agitated vigorously on a rotary shaker for 30–48 hours. These 100 ml. portions of inoculum are then used to inoculate one liter and 12 liter batches of the same medium in 2 liter and 20 liter glass fermentors. The inoculated mash is aerated with sterile air while growth is continued for 40–55 hours. These batches of inoculum are used to inoculate tank fermentors.

Tank Fermentation for BM123α

For the production of BM123α in tank fermentors the following medium is regularly used:
Bacto-peptone 10.0 gm.
Dextrose 20.0 gm.
Molasses 20.0 gm.
L-Histidine 0.4 gm.
Ferric ammonium citrate 0.1 gm.
Calcium carbonate 1.0 gm.
Water to 1,000 ml.
Adjust medium to pH 7.2 with NaOH Each tank is inoculated with 3 to 10% of inoculum made as described above. Aeration is supplied at the rate of 0.2–0.8 liter of sterile air per liter of broth per minute and the fermenting mixture is agitated by an impeller driven at 200–400 r.p.m. The temperature is maintained at 25°–29° C., usually at 28° C. The fermentation is ordinarily continued for 120–190 hours, at which time the mash is harvested.

Fermentation Process Selected to Produce Primarily BM123β and BM123γ

Cultivation of *Nocardia sp.* NRRL 8050 may be carried out in a wide variety of liquid culture media. Media which are useful for the production of the novel antibiotics include as assimilable source of carbon such as starch, sugar, molasses, glycerol, etc.; an assimilable source of nitrogen such as protein, protein hydrolyzate, polypeptides, amino acids, corn steep liquor, etc.; and inorganic anions and cations, such as potassium, magnesium, calcium, ammonium, sulfate, carbonate, phosphate, chloride, etc. Trace elements such as boron, molybdenum, copper, etc.; are supplied as impurities of other constituents of the media. Aeration in tanks and bottles is provided by forcing sterile air through or onto the surface of the fermenting medium. Further agitation in tanks is provided by a mechanical impeller. An antifoaming agent, such as Hodag FD82 may be added as needed.

Inoculum Preparation for BM123β and BM123γ

Primary shaker flask inoculum of *Nocardia sp.* NRRL 8050 is prepared by inoculating 100 milliliters of sterile liquid medium in 500 milliliter flasks with scrapings or washings of spores from an agar slant of the culture. The following medium is ordinarily used:
Bacto-tryptone 5 gm.
Yeast extract 5 gm.
Beef extract 3 gm.
Glucose 10 gm.
Water to 1000 ml.

The flasks were incubated at a temperature from 25°–29° C., preferably 28° C. and agitated vigorously on a rotary shaker for 30 to 48 hours. The inocula are then transferred into sterile screw cap culture tubes and stored at below 0° F. This bank of vegetative inoculum is used instead of slant scrapings for inoculation of additional shaker flasks in preparation of this first stage of inoculum.

These first stage flask inocula are used to seed 12 liter batches of the same medium in 20 liter glass fermentors. The inoculum mash is aerated with sterile air while growth is continued for 30 to 48 hours.

The 12 liter batches of second stage inocula are used to seed tank fermentors containing 300 liters of the following sterile liquid medium to produce the third and final stage of inoculum:

Meat solubles 15 gm.
Ammonium sulfate 3 gm.
Potassium phosphate, dibasic 3 gm.
Calcium carbonate 1 gm.
Magnesium sulfate heptahydrate 1.5 gm.
Glucose 10 gm.
Water to 1000 ml.
The glucose is sterilized separately.

The third stage inoculum is aerated at 0.4 to 0.8 liters of sterile air per liter of broth per minute, and the fermenting mixture is agitated by an impeller driven at 150–300 revolutions per minute. The temperature is maintained at 25°–29° C., usually 28° C. The growth is continued for 48 to 72 hours, at which time the inoculum is used to seed a 3000 liter tank fermentation.

Tank Fermentation for BM123$\beta$ and BM123$\gamma$

For the production of BM123$\beta$ and BM123$\gamma$ in tank fermentors, the following fermentation medium is preferably used:

Meat solubles 30 gm.
Ammonium sulfate 6 gm.
Potassium phosphate, dibasic 6 gm.
Calcium carbonate 2 gm.
Magnesium sulfate heptahydrate 3 gm.
Glucose 20 gm.
Water to 1000 ml.
The glucose is sterilized separately.

Each tank is inoculated with 5 to 10% of third stage inoculum made as described under inoculum preparation. The fermenting mash is maintained at a temperature of 25°–28° C. usually 26° C. The mash is aerated with sterile air at a rate of 0.3–0.5 liters of sterile air per liter of mash per minute and agitated by an impeller driven at 70 to 100 revolutions per minute. The fermentation is allowed to continue from 65–90 hours and the mash is harvested.

The invention will be described in greater detail in conjunction with the following specific examples.

EXAMPLE 1

Inoculum Preparation for BM123$\alpha$

A typical medium used to grow the primary inoculum was prepared according to the following formula:

Beef extract 3.0 gm.
Bacto-tryptone 5.0 gm.
Yeast extract 5.0 gm.
Starch 24.0 gm.
Dextrose 1.0 gm.
Water to 1,000 ml.
Adjust medium to pH 7.0 with NaOH Washed or scraped spores from an agar slant of Nocardia sp. NRRL 8103 were used to inoculate two 500 ml. flasks containing 100 ml. each of the above sterile medium. The flasks were placed on a rotary shaker and agitated vigorously for 48 hours at 28° C. The resulting flask inoculum was transferred to a 5 gallon glass fermentor containing 12 liters of sterile medium. The mash was aerated with sterile air while growth was carried out for about 48 hours, after which the contents were used to seed a 100 gallon tank fermentor containing 290 liters of sterile fermentation medium.

EXAMPLE 2

Fermentation Employing Nocardia sp. NRRL 8103 and Medium Favoring the Production of BM123$\alpha$ A fermentation medium was prepared according to the following formula:

Bacto-peptone 10.0 gm.
Dextrose 20.0 gm.
Molasses 20.0 gm.
L-Histidine 0.4 gm.
Ferric ammonium citrate 0.1 gm.
Calcium carbonate 1.0 gm.
Water to 1,000 ml.
Adjust medium to pH 7.2 with NaOH The fermentation medium was sterilized at 120° C. with steam at 20 lbs. pressure for 60 minutes. The pH of the medium after sterilization was 6.6. Five hundred and sixty liters of sterile medium in two 100 gallon tank fermentors were inoculated with 12 liters each of inoculum prepared as described in Example 1. The fermentation was carried out at 28° C. using Hodag FD82 as a defoaming agent. Aeration was supplied at the rate of 0.4 liter of sterile air per liter of mash per minute. The mash was agitated by impellers driven at 200–290 revolutions per minute. At the end of approximately 139 hours of fermentation time the mash was harvested.

EXAMPLE 3

Inoculum preparation for BM123$\beta$ and BM123$\gamma$

A typical medium used to grow the first and second stages of inoculum was prepared according to the following formula:

Bacto-tryptone 5 gm.
Yeast extract 5 gm.
Beef extract 3 gm.
Glucose 10 gm.
Water to 1000 ml.

Two 500 milliliter flasks each containing 100 milliliters of the above sterile medium were inoculated with 5 milliliters each of a frozen vegetative inoculum from Nocardia sp. NRRL 8050. The flasks were placed on a rotary shaker and agitated vigorously for 48 hours at 28° C. The resulting flask inoculum was transferred to a 5 gallon glass fermentor containing 12 liters of the above sterile medium. The mash was aerated with sterile air while growth was carried out for about 48 hours, after which the contents were used to seed a 100 gallon tank fermentor containing 300 liters of the following sterile liquid medium:

Meat solubles 15 gm.
Ammonium sulfate 3 gm.
Potassium phosphate, dibasic 3 gm.
Calcium carbonate 1 gm.
Magnesium sulfate heptahydrate 1.5 gm.
Glucose 10 gm.
Water to 1000 ml.
The glucose is sterilized separately.

The third stage of inoculum mash was aerated with sterile air sparged into the fermentor at 0.4 liters of air per liter of mash per minute. Agitation was supplied by a driven impeller at 240 revolutions per minute. The mash was maintained at 28° C. and Hodag FD82 was used as a defoaming agent. After 48 hours of growing time the inoculum mash was used to seed a 3000 liter fermentation.

EXAMPLE 4

Fermentation Employing Nocardia sp. NRRL 8050 and Medium Favoring the Production of BM123β and BM123γ

A fermentation medium was prepared according to the following formula:
Meat solubles 30 gm.
Ammonium sulfate 6 gm.
Potassium phosphate, dibasic 6 gm.
Calcium carbonate 2 gm.
Magnesium sulfate heptahydrate 3 gm.
Glucose 20 gm.
Water to 1000 ml.
The glucose is sterilized separately.

The fermentation medium was sterilized at 120° C. with steam at 20 pounds pressure for 60 minutes. The pH of the medium after sterilization was 6.9. Three thousand liters of sterile medium in a 4000 liter tank fermentor was inoculated with 300 liters of inoculum such as described in Example 3, and the fermentation was carried out at 26° C. using Hodag FD82 as a defoaming agent. Aeration was supplied at the rate of 0.35 liter of sterile air per liter of mash per minute. The mash was agitated by an impeller driven at 70–72 revolutions per minute. At the end of 67 hours of fermentation time the mash was harvested.

EXAMPLE 5

Isolation of BM123α

A fermentation was carried out as described in Example 2. Five hundred liters of fermented mash having a pH of 6.8 was filtered using 5 kg. of diatomaceous earth as a filter aid. The cake was washed with about 75 liters of water and discarded. Sodium fluoride (1 kg.) was added to the combined filtrate and wash and the mixture was stirred for one hour. The resulting suspension was filtered using about 5.75 kg. of diatomaceous earth as a filter aid and the cake was washed with about 5 liters of water and discarded. The combined filtrate and wash (580 liters, pH 6.7) was allowed to percolate through a column of 10 liters of Amberlite IRC-50 (a methacrylic acid-divinyl benzene ion exchange resin available from Rohm & Haas Co.) ($Na^+$; 16–50 mesh) in a 6 × 60 inch glass column. The charged column was washed with 40 liters of water. The BM123α was eluted by passing 120 liters of 0.3N $H_2SO_4$ through the column. The initial 9 liters of eluate was discarded. The remaining eluate was adjusted to pH 6.0 with solid $Ba(OH)_2$ and the precipitated barium sulfate was removed by filtration. The clear filtrate was concentrated in vacuo to about 20 liters which was then slowly percolated through a 12 liter bed volume column of granular Darco activated carbon (a granular activated carbon available from ICI of U.S.) (20–40 mesh). The charged column was washed with 40 liters of water and eluted with 60 liters of 50% aqueous methanol. The column eluate was concentrated to about 4 liters of aqueous solution and lyophilized to give 104.1 gms. of white solid BM123α as the sulfate salt.

The BM123α so prepared does not possess a definite melting point, gradual decomposition starting in the vicinity of 200° C. Microanalysis of a sample quilibrated for 24 hours in a 73° F. atmosphere containing 60% relative humidity gave C, 32.10%; H, 5.64%; N, 10.80%; S, 4.45%; loss on drying 12.52%. The BM123α was transparent to light in the region 220 to 340 nm when run in 90% methanol at 200 mcg./ml. BM123α had a specific rotation of $[\alpha]_D^{25°} = +40°$ (C=1.1 in $H_2O$). The BM123α exhibited characteristic absorption in the infrared region of the spectrum at the following wavelengths: 780, 815, 950, 1050, 1110, 1250, 1340, 1395, 1560, 1670, 1705, 2950, and 3330 $cm^{-1}$. A standard infrared absorption spectrum of BM123α prepared in a KBr pellet is shown in FIG. 1 of the accompanying drawings.

EXAMPLE 6

Isolation of BM123β and BM123γ

A 3000 liter portion of fermentation mash prepared as described in Example 4, pH 4.3, was adjusted to pH 7.0 with sodium hydroxide and filtered using 5% diatomaceous earth as a filter aid. The cake was washed with about 100 liters of water and discarded. The combined filtrate and wash was pumped upward through three parallel 8¼ × 48 stainless steel columns each containing 15 liters of CM Sephadex C-25 [$Na^+$] resin. The charged columns were washed with a total of about 390 liters of water and then developed with 200 liters of 1% aqueous sodium chloride followed by 560 liters of 5% aqueous sodium chloride. The 5% aqueous sodium chloride eluate was clarified by filtration through diatomaceous earth and the clarified filtrate passed through a 9 × 60 glass column containing 25 liters of granular Darco activated carbon (20–40 mesh). The charged column was washed with 120 liters of water and then developed with 120 liters of 15% aqueous methanol followed by 340 liters of 50% aqueous methanol and then 120 liters of 50% aqueous acetone. The 15% aqueous methanol eluate was concentrated in vacuo to about 7 liters of an aqueous phase and the pH adjusted from 4.5 to 6.0 with Amberlite IR-45 ($OH^-$) resin (a weakly basic polystyrene-polyamine type anion exchange resin). The resin was removed by filtration and the filtrate was concentrated in vacuo to about 1 liter and then lyophilized to give 38 grams of material consisting primarily of BM123β along with a small amount of BM123γ (primarily BM123γ$_2$). The 50% aqueous methanol eluate was adjusted from pH 4.65 to 6.0 with Amberlite IR-45 ($OH^-$) resin. The resin was removed by filtration and the filtrate was concentrated in vacuo to about 6.3 liters and then lyophylized to give 213 grams of material consisting primarily of BM123γ. The 50% aqueous acetone eluate was adjusted from pH 4.0 to 6.0 with Amberlite IR-45 ($OH^-$) resin. The resin was removed by filtration and the filtrate was concentrated in vacuo to about 1.5 liters and then lyophylized to give 56 grams of impure BM123γ.

EXAMPLE 7

Further purification of BM123β; Isolation of BM123β$_1$

A slurry of CM Sephadex C-25 [$NH_4^+$] in 3% aqueous ammonium chloride was poured into a 2.6 centimeter diameter glass column to a resin height of approximately 57 centimeters. The excess of 3% aqueous ammonium chloride was drained away and a 5.0 gram sample of BM123β prepared as described in Example 6 was dissolved in about 10 milliliters of 3% aqueous ammonium chloride and applied to the column. The column was then eluted with a gradient between 4 liters each of 3% and 6% aqueous ammonium chloride. Fractions of about 70 milliliters each were collected automatically every 15 minutes. Antibiotic BM123β was located by monitoring the column effluent in the ultraviolet and by bioautography of dipped paper disks on large agar plates seeded with *Klebsiella pneumoniae* strain AD. The majority of BM123β was located between fractions 51-67 inclusive; the initial fractions (51-58) contained essentially pure BM123β$_1$ whereas the later fractions (59-67) contained a mixture of BM123β$_1$ and BM123β$_2$.

Two hundred fifty milliliters of granular Darco activated carbon (20-40 mesh) was suspended in water, transferred to a glass column, allowed to settle and the excess water was allowed to drain away. Fractions 51-58 inclusive from the above CM Sephadex chromatography were combined and passed through the granular carbon column. The charged column was washed with 1 liter of water and then developed with 1.5 liters of 20% aqueous methanol. The aqueous methanol eluate was concentrated to an aqueous phase in vacuo and lyophilized to give 1.24 grams of white amorphous BM123β$_1$ as the hydrochloride salt.

Antibiotic BM123β$_1$ does not possess a definite melting point, but gradual decomposition starts in the vicinity of 200° C. Microanalysis of a sample equilibrated for 24 hours in a 72° F. atmosphere containing 23% relative humidity gave C, 39.29%; H, 6.33%; N, 16.58%; Cl(ionic), 13.28%; loss on drying, 6.90%. In methanol BM123β$_1$ gave a U.V. absorption maximum at 286 nm with $E_{1cm}^{1\%} = 260$. The position of this maximum did not change with pH. BM123β$_1$ had a specific rotation of $[\alpha]_D^{25°} = +67°$ (C=1.0 in water).

Figure 4:
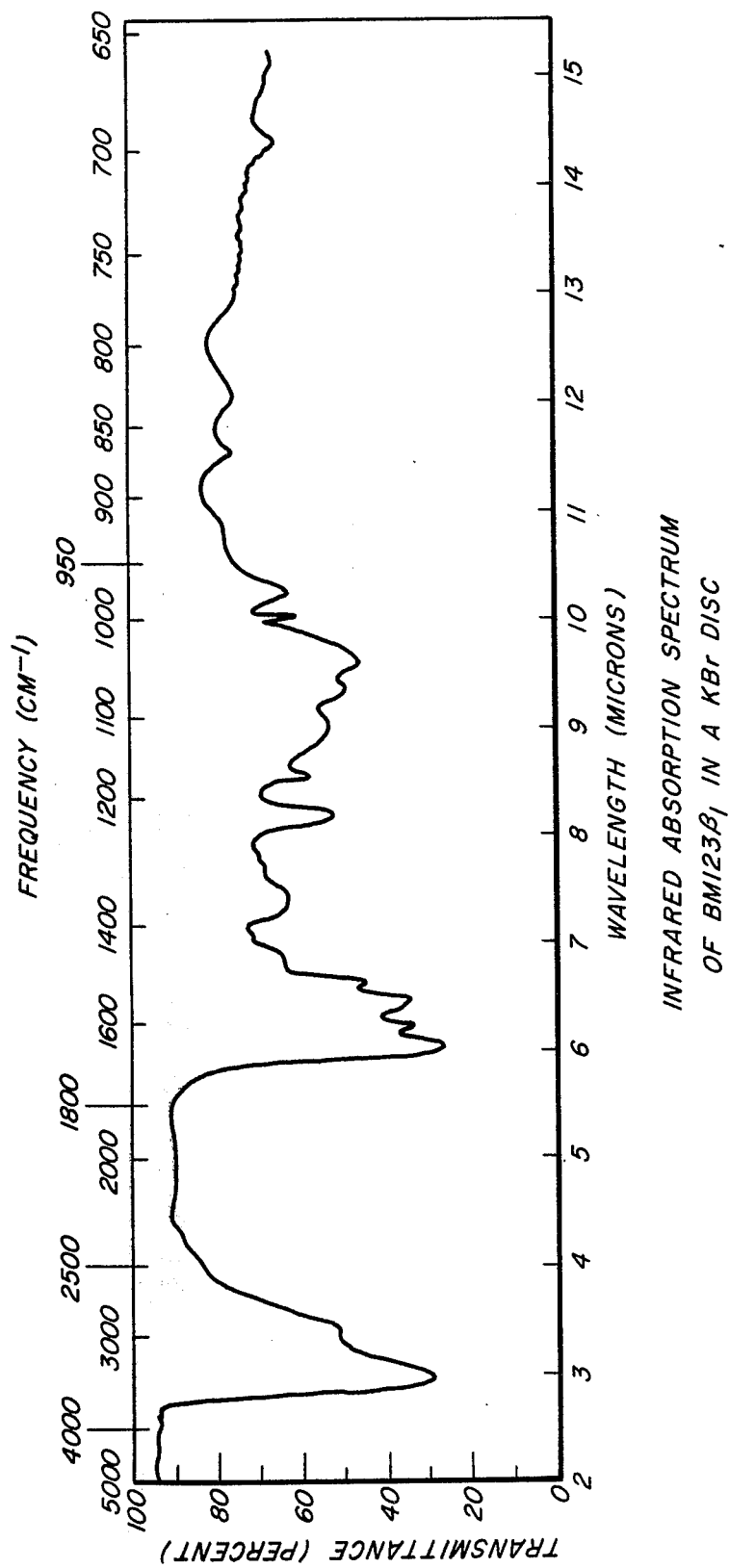

Antibiotic BM123β$_1$ exhibited characteristic absorption in the infrared region of the spectrum at the following wavelengths: 830, 870, 930, 975, 1040, 1070, 1105, 1175, 1220, 1360, 1460, 1505, 1550, 1600, 1650, 2900, 3050 and 3350 cm$^{-1}$. A standard infrared absorption spectrum of BM123β$_1$ prepared in a KBr pellet is shown in FIG. 4 of the accompanying drawings. A standard proton magnetic resonance spectrum of BM123β$_1$ determined on a D$_2$O solution in a 100 megacycle spectrometer is shown in FIG. 7 of the accompanying drawings.

Fractions 59-67 inclusive from the above CM Sephadex chromatography were combined and passed through a 200 milliliter bed volume granular carbon column. The charged column was then washed with 1 liter of water and then developed with 1.5 liters of 20% aqueous methanol. The aqueous methanol eluate was concentrated to an aqueous phase in vacuo and lyophilized to give 0.83 grams of white amorphous BM123β as the hydrochloride salt.

Antibiotic BM123β does not possess a definite melting point, but gradual decomposition starts in the vicinity of 200° C. Microanalysis of a sample equilibrated for 24 hours in a 72° F. atmosphere containing 23% relative humidity gave C, 38.81%; H, 6.19%; N, 16.52%; Cl(ionic), 13.41%; loss on drying, 7.32%. In methanol BM123β gave a U.V. absorption maximum at 286 nm with $E_{1cm}^{1\%} = 255$. The position of this maximum did not change with pH. BM123β had a specific rotation of $[\alpha]_D^{25°} = +63°$ (C = 1.06 in water).

Figure 2:
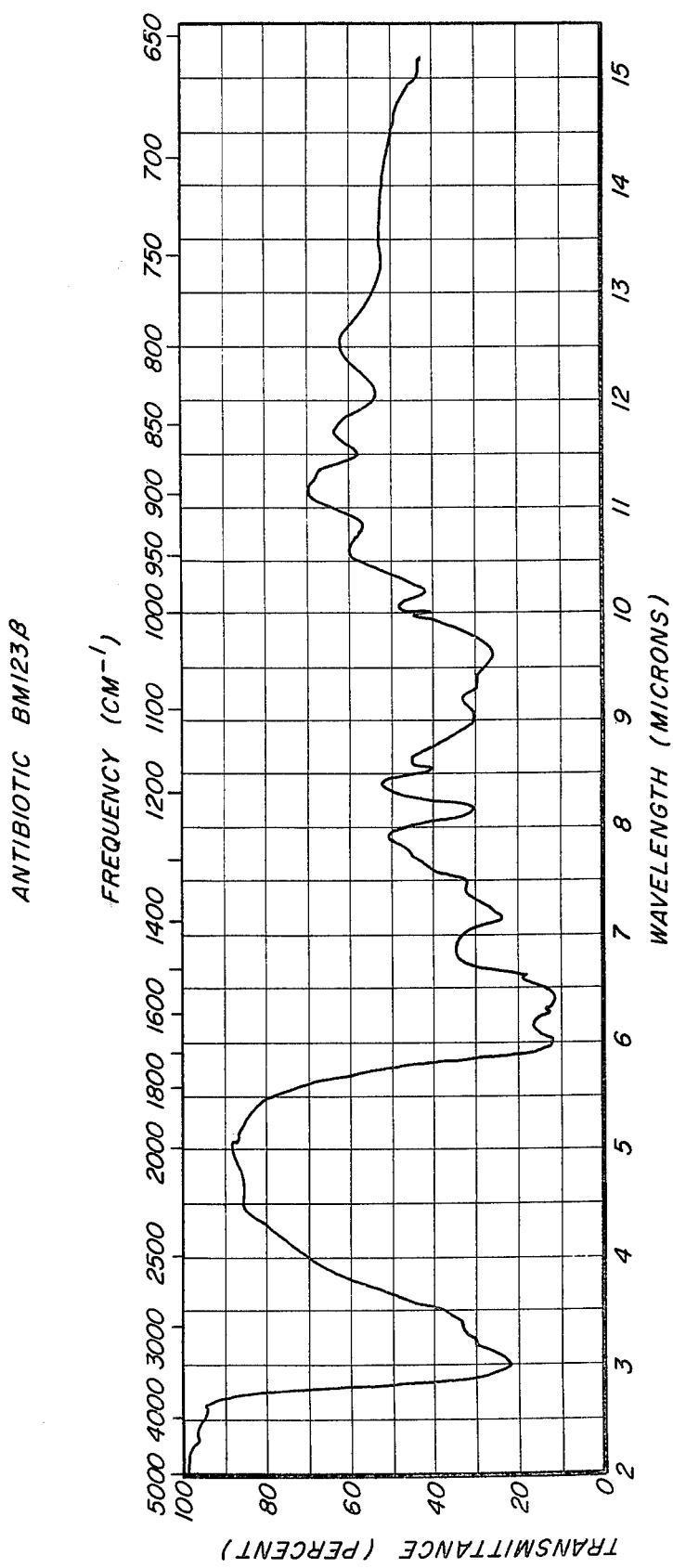

Antibiotic BM123β exhibited characteristic absorption in the infrared region of the spectrum at the following wavelengths: 830, 870, 930, 975, 1040, 1070, 1105, 1175, 1220, 1360, 1460, 1505, 1550, 1600, 1650, 2925, 3050 and 3025 cm$^{-1}$. A standard infrared absorption spectrum of BM123β prepared in a KBr pellet is shown in FIG. 2 of the accompanying drawings.

EXAMPLE 8

Further Purification of BM123γ

A slurry of CM Sephadex C-25 [NH$_4^+$] in 2% aqueous ammonium chloride was poured into a 2.6 centimeter diameter glass column to a resin height of approximately 62 centimeters. The excess 2% aqueous ammonium chloride was drained away and a 5.0 gram sample of BM123γ prepared as described in Example 9 was dissolved in about 10 milliliters of 2% aqueous ammonium chloride and applied to the column. The column was then eluted with a gradient between 6 liters each of 2% and 4% aqueous ammonium chloride. Fractions of about 75 milliliters each were collected automatically every 15 minutes. Antibiotic BM123γ was located by monitoring the column effluent in the ultraviolet and by bioautography of dipped paper disks on large agar plates seeded with *Klebsiella pneumoniae* strain AD. The majority of BM123γ was located between fractions 71-107 inclusive.

One hundred thirty milliliters of granular Darco activated carbon (20-40 mesh) was suspended in water, transferred to a glass column, allowed to settle and the excess water was allowed to drain away. Fractions 84-96 inclusive from the above CM Sephadex chromatography were combined and passed through the granular carbon column. The charged column was washed with 600 milliliters of water and then developed with 1 liter of 20% aqueous methanol followed by 1 liter of 50% aqueous acetone. These eluates, both of which contained BM123γ, were concentrated to aqueous phases in vacuo and lyophilized to give a total of 886 milligrams of BM123γ as the hydrochloride salt. A microanalytical sample was obtained by subjecting the above material to a repeat of the above process.

Antibiotic BM123γ does not possess a definite melting point, but gradual decomposition starts in the vicinity of 200° C. Microanalysis of a sample equilibrated for 24 hours in a 72° F. atmosphere containing 23% relative humidity gave C, 39.44%; H, 6.10%; N, 16.19%; Cl(ionic), 11.54%; loss on drying, 8.19%. In water BM123γ gave a U.V. absorption maximum at 286 nm with $E_{1cm}^{1\%} = 250$. The position of this maximum did not change with pH. BM123γ had a specific rotation of $[\alpha]_D^{25°} = +71°$ (C = 0.97 in water).

Figure 3:
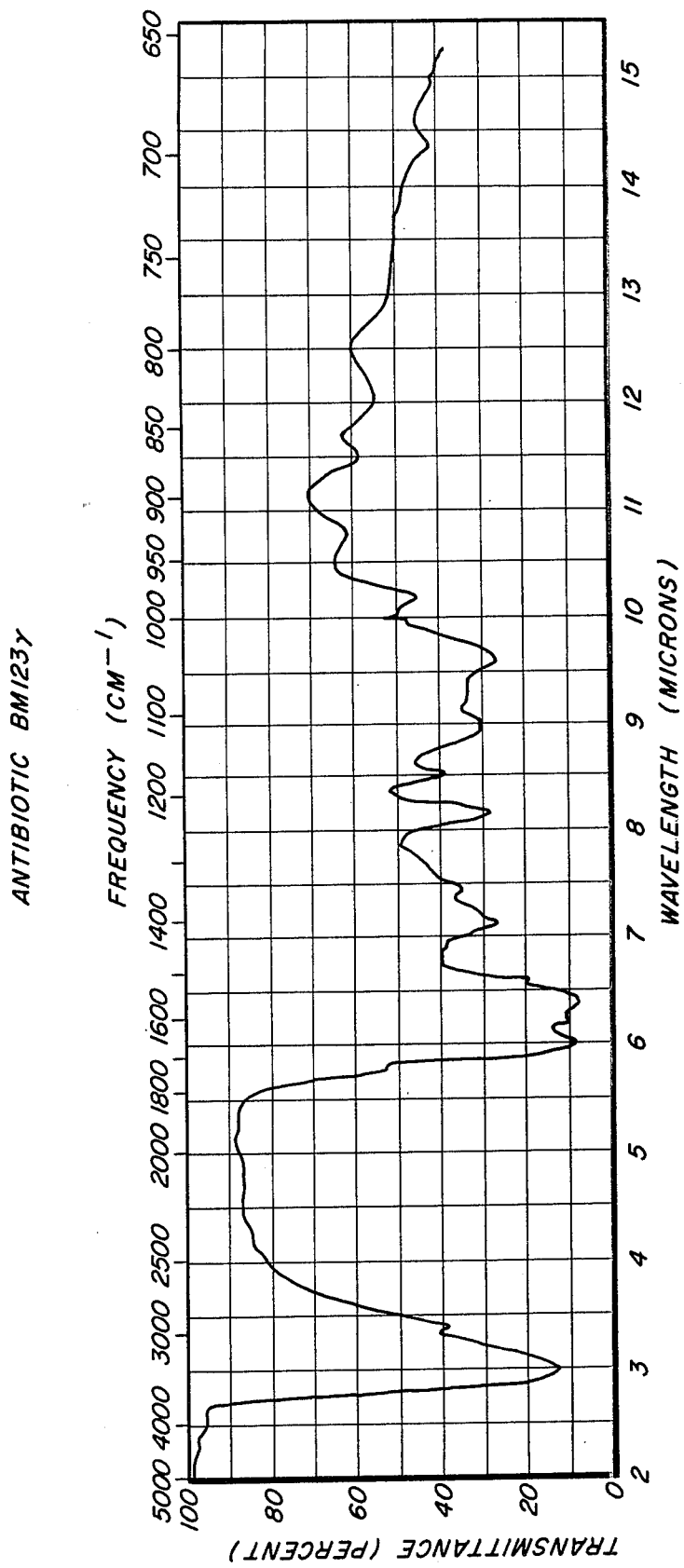

Antibiotic BM123γ exhibited characteristic absorption in the infrared region of the spectrum at the following wavelengths: 770, 830, 870, 930, 980, 1035, 1105, 1175, 1225, 1300, 1340, 1370, 1460, 1510, 1555, 1605, 1660, 1740, 2950 and 3350 cm$^{-1}$. A standard infrared absorption spectrum of BM123γ prepared in a KBr pellet is shown in FIG. 3 of the accompanying drawings.

EXAMPLE 9

Isolation of BM123γ$_1$

A slurry of CM Sephadex C-25 [Na$^+$] in 2% aqueous sodium chloride was poured into a 2.6 centimeter diameter glass column to a resin height of approximately 70 centimeters. The excess 2% aqueous sodium chloride was drained away and 4.11 gram of a sample containing primarily BM123γ$_1$ along with some BM123γ$_2$ and other impurities, prepared as described in Example 6, was dissolved in about 10 milliliters of 2% aqueous sodium chloride and applied to the column. The column was then eluted with a gradient between 4 liters each of 2% and 4% aqueous sodium chloride. Fractions of about 75 milliliters each were collected automatically every 15 minutes. Antibiotic BM123γ was located by monitoring the column effluent in the ultraviolet and by bioautography of dipped paper disks on large agar plates seeded with *Klebsiella pneumoniae* strain AD. The majority of BM123γ was located between fractions 64–90 inclusive; the initial fractions (64–80) contained a mixture of BM123γ$_1$ and BM123γ$_2$ whereas the later fractions (81–90) contained essentially pure BM123γ$_1$.

One hundred milliliters of granular Darco activated carbon (20–40 mesh) was suspended in water, transferred to a glass column, allowed to settle and the excess water was allowed to drain away. Fractions 81–90 inclusive from the above CM Sephadex chromatography were combined and passed through the granular carbon column. The charged column was washed with 500 milliliters of water and then developed with 500 milliliters of 10% aqueous methanol followed by 1 liter of 50% aqueous methanol. The 50% aqueous methanol eluate, which contained the majority of BM123γ$_1$, was adjusted from pH 5.9 to 6.0 with Amberlite IR-45(OH$^{-1}$) resin. The resin was removed by filtration and the filtrate was concentrated in vacuo to an aqueous phase and lyophilized to give 294 milligrams of white amorphous BM123γ$_1$ as the hydrochloride salt.

Antibiotic BM123γ$_1$ does not possess a definite melting point, but gradual decomposition starts in the vicinity of 200° C. Microanalysis of a sample equilibrated for 24 hours in a 70° F. atmosphere containing 60% relative humidity gave C, 37.84%; H, 5.73%; N, 15.58%; Cl(ionic), 10.01%; loss on drying 10.45%. In methanol BM123γ$_1$ gave a U.V. absorption maximum at 286 nm with $E_{1cm}^{1\%} = 225$. The position of this maximum did not change with pH. BM123γ$_1$ had a specific rotation of +55° (C=0.803 in water).

Figure 5:
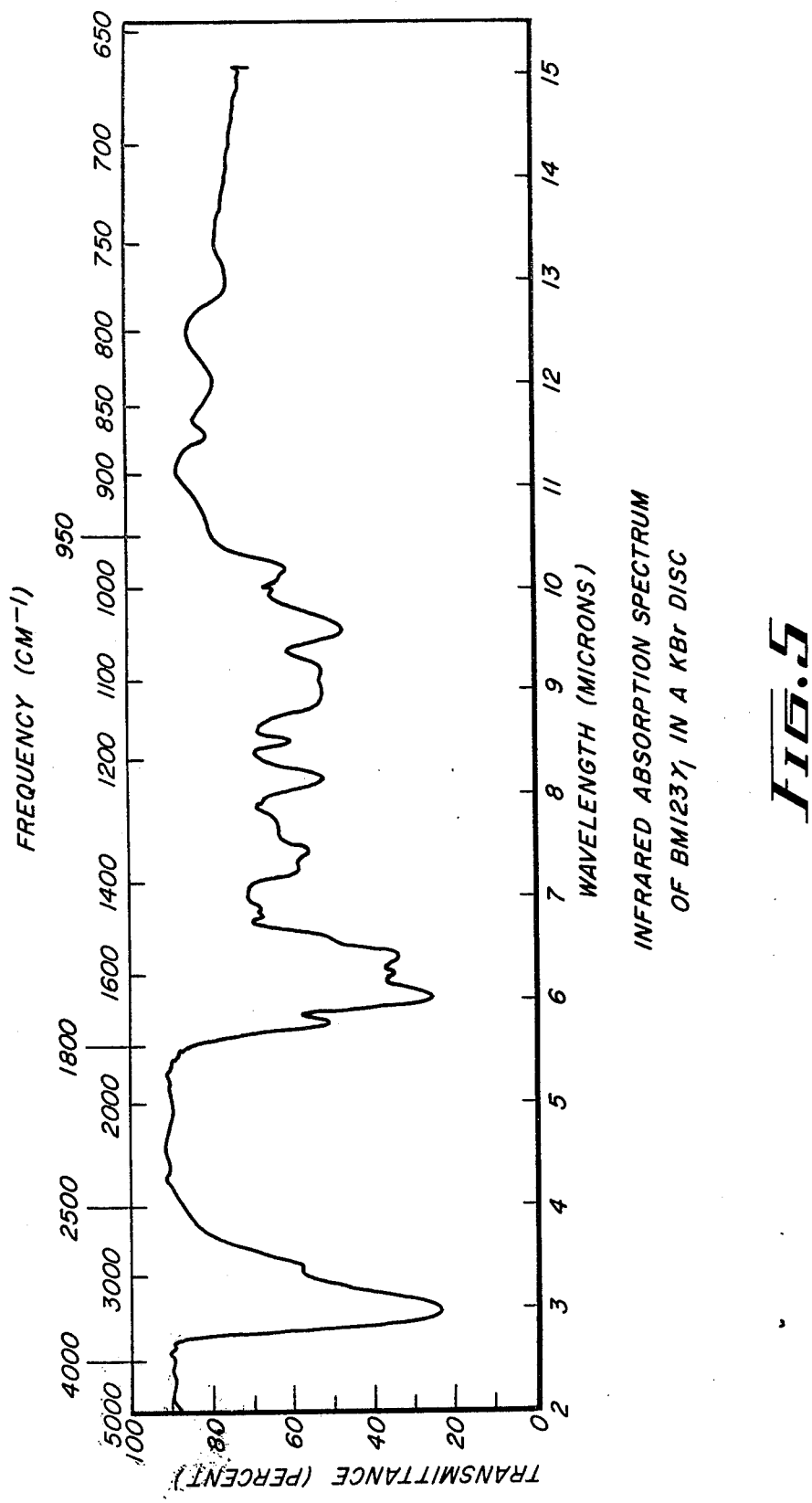

Antibiotic BM123γ$_1$ exhibited characteristic absorption in the infrared region of the spectrum at the following wavelengths: 770, 830, 870 930, 980, 1045, 1080, 1110, 1125, 1175, 1225, 1305, 1345, 1380, 1465, 1515, 1560, 1605, 1660, 1730, 2950 and 3350 cm$^{-1}$. A standard infrared absorption spectrum of BM123γ$_1$ prepared in a KBr pellet is shown in FIG. 5 of the accompanying drawings. A standard proton magnetic resonance spectrum of BM123γ$_1$ determined on a D$_2$O solution in a 100 megacycle spectrometer is shown in FIG. 8 of the accompanying drawings.

EXAMPLE 10

Isolation of BM123γ$_2$

A 25 gram sample containing primarily BM123γ$_2$ and BM123β, prepared as described in Example 6, was dissolved in about 120 milliliters of 2% aqueous sodium chloride and applied to a column containing 1800 ml. of CM Sephadex C-25 [Na$^+$] in 2% aqueous sodium chloride. The column was then eluted with a gradient between 20 liters each of 2 and 4% aqueous sodium chloride. The initial 12 liters of eluate was collected in a large bottle and discarded. Thereafter fractions of about 800 milliliters each were collected automatically every 40 minutes. Antibiotic BM123γ was located by monitoring the column fractions in the ultraviolet. The majority of BM123γ was located between fractions 7–18 inclusive; the initial fractions (7–15) contained essentially pure BM123γ$_2$ and the later fractions (16–18) contained a mixture of BM123γ$_1$ and BM123γ$_2$.

Six hundred milliliters of granular Darco activated carbon (20–40 mesh) was suspended in water, transferred to a glass column, allowed to settle and the excess water was allowed to drain away. Fractions 7–15 inclusive from the above CM Sephadex chromatography were combined and passed through the granular carbon column. The charged column was washed with 3 liters of water and then developed with 3 liters of 10% aqueous methanol followed by 6 liters of 50% aqueous methanol. The 10% aqueous methanol eluate was adjusted from pH 5.8 to 6.0 with Amberlite IR 45 (OH$^-$) resin. The resin was removed by filtration and the filtrate was concentrated in vacuo to an aqueous phase and lyophilized to give 595 milligrams of white amorphous BM123γ$_2$ as the hydrochloride salt. The 50% aqueous methanol eluate was adjusted from pH 4.6 to 6.1 with Amberlite IR 45 (OH$^-$) resin. The resin was removed by filtration and the filtrate was concentrated in vacuo to an aqueous phase and lyophilized to give 3.645 grams of slightly less pure white amorphous BM123γ$_2$ as the hydrochloride salt.

Antibiotic BM123γ$_2$ does not possess a definite melting point, but gradual decomposition starts in the vicinity of 200° C. Microanalysis of a sample equilibrated for 24 hours in a 70° F. atmosphere containing 60% relative humidity gave C, 36.14%; H, 5.67; N, 15.1%; Cl(ionic), 11.11%; loss on drying 10.87%. In methanol BM123γ$_2$ gave a U.V. absorption maximum at 286 nm with $E_{1cm}^{1\%} = 220$. The position of this maximum did not change with pH. BM123γ$_2$ had a specific rotation of +60° (C=0.851 in water).

Antibiotic BM123γ$_2$ exhibited characteristic absorption in the infrared region of the spectrum at the following wavelengths: 770, 830, 950, 980, 1035, 1110, 1175, 1225, 1285, 1345, 1380, 1470, 1515, 1560, 1605, 1660, 1755, 2950 and 3350 cm$^{-1}$. A standard infrared absorption spectrum of BM123γ$_2$ prepared in a KBr pellet is shown in FIG. 6 of the accompanying drawings. A standard proton magnetic resonance spectrum of BM123γ$_2$ determined on a D$_2$O solution in a 100 megacycle spectrometer is shown in FIG. 9 of the accompanying drawings.

EXAMPLE 11

Paper Partition and Thin Layer Chromatography of BM123α,β and γ

The antibacterial agents can be distinguished by paper chromatography. For this purpose Whatman No. 1 strips were spotted with a water or methanol solution of the substances and equilibrated for 1 to 2 hours in the presence of both upper and lower phases. The strips were developed overnight with the lower (organic) phase obtained from mixing 90% phenol:m-cresol:acetic acid:pyridine:water (100:25:4:4:75 by volume). The developed strips were removed from the chromatographic chamber, air dried for 1 to 2 hours, washed with ether to remove residual phenol and bioautographed on large agar plates seeded with *Klebsiella pneumoniae* strain AD. Representative Rf values are listed in Table VIII below:

TABLE VIII

| Component | Rf |
| --- | --- |
| BM123γ | 0.85 |
| BM123β | 0.50, 0.70 |
| BM123α | 0.20 |

BM123β was composed of a major antibiotic (Rf = 0.50) called BM123β₁ and a minor antibiotic (Rf = 0.70) called BM123β₂.

The BM123 antibiotics can also be distinguished by thin layer chromatography. For this purpose precoated Cellulose F plates (0.10 millimeters thick), a form of thick layer cellulose supplied by EM Laboratories Inc., Elmsford, N.Y. were spotted with a water solution of the substance to be chromatographed (about 20–40 micrograms per spot). The plates were developed overnight with the solvent obtained by mixing 1-butanol:water:pyridine:acetic acid (15:12:10:1 by volume). The developed plates were removed from the chromatographic chamber and air dried for about 1 hour. The antibiotics were detected by using either standard ninhydrin or Sakaguchi spray reagents. Representative Rf values are listed in Table IX below:

TABLE IX

| Component | Rf |
|---|---|
| BM123γ | 0.17, 0.23 |
| BM123β | 0.08, 0.14 |
| BM123α | 0.05 |

Both BM123β and γ were a mixture of two components using this system. BM123β was composed of a major component (Rf = 0.08) which was BM123β₁ and a minor component (Rf = 0.14) which was BM123β₂. The less polar component of BM123γ (Rf = 0.23) was named BM123γ₁ and the more polar component (Rf = 0.17) was named BM123γ₂.

We claim:

1. A compound selected from the group consisting of antibacterial BM123α of the formula:

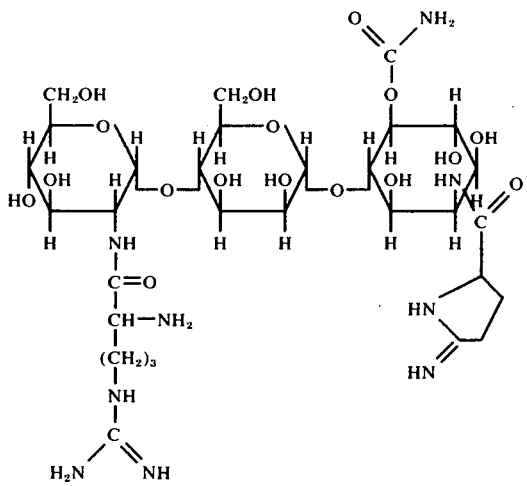

and the pharmacologically acceptable acid-addition salts thereof.

2. Antibacterial BM123β, a composition which
    a. is effective in inhibiting the growth of bacteria and in its substantially pure form consisting essentially of a mixture of BM123β₁ and BM123β₂;
    b. has an optical rotation $[\alpha]_D^{25°} = +63°$ (C=1.06 in water);
    c. has the following elemental analysis (percent): C, 38.81; H, 6.19; N, 16.52; Cl (ionic), 13.41; loss on drying, 7.32; and
    d. had a characteristic infrared absorption spectrum as shown in FIG. 2 of the accompanying drawings.

3. A compound selected from the group consisting of antibacterial BM123β₁ of the formula:

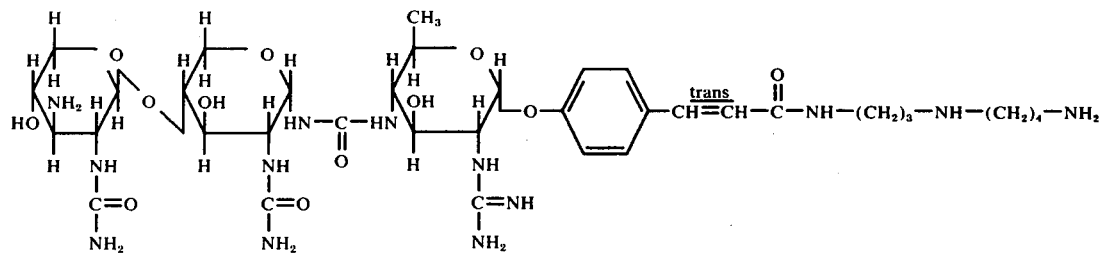

and the pharmacologically acceptable acid-addition salts thereof.

4. A compound selected from the group consisting of antibacterial BM123γ₁ of the formula:

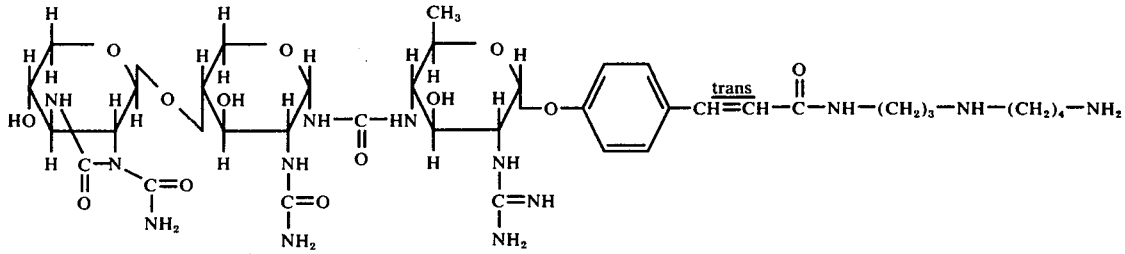

and the pharmacologically acceptable acid-addition salts thereof.

5. A compound selected from the group consisting of antibacterial BM123γ₂ of the formula:

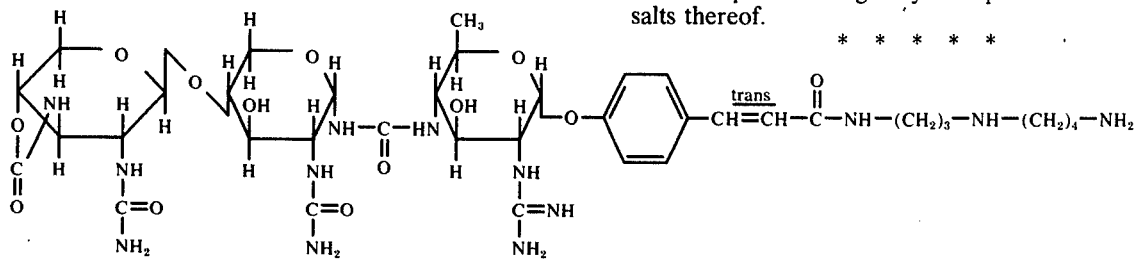
and the pharmacologically acceptable acid-addition salts thereof.
* * * * *